United States Patent
Yu et al.

(10) Patent No.: US 8,246,920 B2
(45) Date of Patent: Aug. 21, 2012

(54) METHOD AND REAGENT TUBE FOR REDUCING REAGENT USAGE

(75) Inventors: Ziyuan Yu, Beijing (CN); Jin Shao, Beijing (CN)

(73) Assignee: Beijing Strong Biotechnologies, Inc., Beijing (CN)

( * ) Notice: Subject to any disclaimer, the term of this patent is extended or adjusted under 35 U.S.C. 154(b) by 436 days.

(21) Appl. No.: 12/503,723

(22) Filed: Jul. 15, 2009

(65) Prior Publication Data

US 2010/0122589 A1    May 20, 2010

(30) Foreign Application Priority Data

Nov. 17, 2008  (CN) .......................... 2008 1 0226804

(51) Int. Cl.
*B01L 9/00* (2006.01)
(52) U.S. Cl. ........ 422/562; 422/549; 422/554; 422/558; 422/560; 422/561
(58) Field of Classification Search .......... 422/560–562, 422/549, 554, 558
See application file for complete search history.

(56) References Cited

U.S. PATENT DOCUMENTS

| 4,076,420 A * | 2/1978 | De Maeyer et al. ............ 356/73 |
| 6,255,101 B1 | 7/2001 | Rousseau et al. |
| 2006/0087650 A1 * | 4/2006 | Shen ............................ 356/244 |

FOREIGN PATENT DOCUMENTS

CA          1015580       8/1977

* cited by examiner

*Primary Examiner* — In Suk Bullock
*Assistant Examiner* — Paul Hyun
(74) *Attorney, Agent, or Firm* — Knobbe, Martens, Olson & Bear, LLP

(57) ABSTRACT

The present invention provides a method for reducing reagent usage, comprising the steps of providing a retainer, at least one group of loopholes being provided on the sidewalls of the retainer; providing a colorimetric glass, adapted to be inserted into the retainer, for receiving the first reagent to be observed through said loopholes; providing a cap, for capping the colorimetric glass and the retainer into a whole, after the colorimetric glass being inserted into the retainer. The present invention mainly uses a reagent tube with a retainer having a new structure, a colorimetric glass and a cap, storing the first reagent only in the colorimetric glass, and the volume of the colorimetric glass is far less than that of the current reagent tube, thus the usage of the reagents can be reduced effectively.

8 Claims, 3 Drawing Sheets

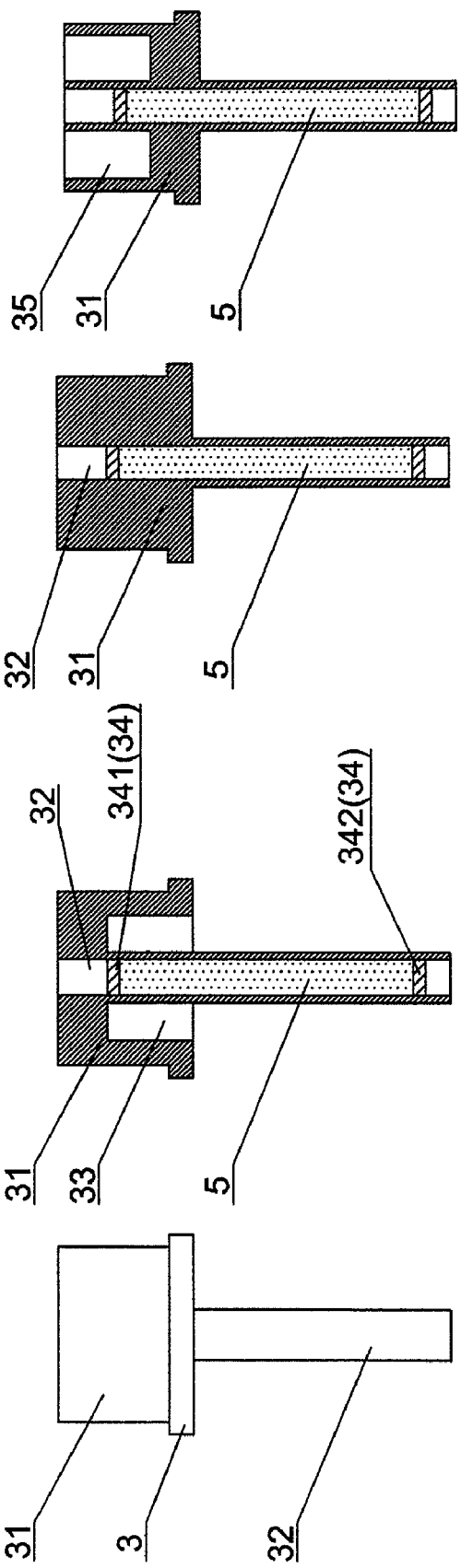

METHOD AND REAGENT TUBE FOR REDUCING REAGENT USAGE

FIELD OF THE INVENTION

The present invention relates to the field of reagent detecting, in particular, to a method and apparatus for reducing reagent usage in the process of reagent detecting.

BACKGROUND OF THE INVENTION

In the current reagent detecting process, basically, the reagent to be detected is filled into a reagent tube with a standard volume and shape, and then reagent detecting is carried on with the reagent tube being put into a detecting instrument to obtain a detecting result. Alternatively, the above reagent to be detected is mixed with one or more other reagents after it is filled into a reagent tube with a standard volume and shape, and then reagent detecting is carried on with the mixed reagent tube being put into a detecting instrument to obtain a detecting result.

However, no matter which of the methods is used, the volume of said reagent tube is unchanged. Taking the calorimetric tube used in the detecting process of glycosylated hemoglobin as an example, firstly, it needs to drop 1.2 ml of R1 reagent into the colorimetric tube, then mix it with pre-treated blood sample, close the cap of the calorimetric tube after mixing, and then place the colorimetric tube into the Diazyme Smart340 Instrument to carry on calorimetric detecting. In the process of detecting, the instrument makes R2 reagent stored in the cap of the calorimetric tube drop into the colorimetric tube to mix it with the previous mixed liquid (mixed liquid of R1 reagent and pre-treated blood), and detecting result of glycosylated hemoglobin is obtained after homogeneous mixing and colorimetric detecting. In the above detecting process, too much R1 and R2 reagents are needed, thus resulting in the increasing of the cost and economic burden to the detector.

SUMMARY OF THE INVENTION

The object of the invention is to provide a method and a reagent tube for reducing reagent usage in the process of reagent detecting.

To achieve such object, the invention provides a method for reducing reagent usage, comprising the steps of: providing a retainer, at least one group of loopholes being provided on the sidewalls of said retainer; providing a calorimetric glass, adapted to be inserted into said retainer, for receiving the first reagent to be observed through said loopholes; providing a cap, for capping the calorimetric glass and the retainer into a whole, after the colorimetric glass being inserted into the retainer.

To achieve such object, the invention also provides a reagent tube for reducing reagent usage, wherein the reagent tube comprises: a retainer, at least one group of loophole being provided on the sidewalls of said retainer; a calorimetric glass, adapted to be inserted into said retainer, for receiving the first reagent to be observed through said loophole; and a cap, for capping the colorimetric glass and the retainer into a whole, after the colorimetric glass being inserted into the retainer.

In the method and reagent tube for reducing reagent usage described in the present invention, said cap comprises a cap body, an inner tube provided at the axis center of the cap body and penetrated through the cap body, and a recess provided at the bottom of the cap body; a second reagent is added in advance and sealed within the inner tube by a sealing means, and said inner tube is adapted to be inserted into the calorimetric glass; the dimension of said recess matches the thicknesses of the upper edges of the colorimetric glass and the retainer, such that the upper edges of the colorimetric glass and the retainer is received in said recess.

In the above method and reagent tube for reducing reagent usage, said sealing means comprises two rubber gaskets, provided at the positions adjacent to the top and bottom of the inner tube respectively.

In the above method and reagent tube for reducing reagent usage of the invention, said loopholes may be in two groups, each group comprises two loopholes, and the projections projected in the axial direction of the said two loopholes are superposed, and preferably, the extension lines of said axis centers of said two groups of loopholes are perpendicular to each other.

In the above method and reagent tube for reducing reagent usage of the invention, said loopholes may also be in three groups, each group comprises two loopholes, and the projections projected in the axial direction of the said two loopholes are superposed, and preferably, the extension lines of said axis centers of said three groups of loopholes form angles of 60° with each other.

In the above method and reagent tube for reducing reagent usage, the material of said retainer is polytetrafluoroethylene, metal or hard plastic, and the said colorimetric glass is of transparent materials, such as UV-transmitting plastic, quartz group materials or light-transmitting plastic.

With the above technical solutions of the invention, the following technical effects can be achieved:

The present invention mainly uses a reagent tube with a new structure of a retainer, a calorimetric glass and a cap, storing the first reagent only in the calorimetric glass, and the volume of the colorimetric glass is far less than that of the current reagent tube, thus the usage of the first reagent can be reduced greatly, and because the second reagent needs to mix with the first reagent in a certain proportion, the usage of the second reagent also can be reduced greatly. After comparison with experiments, in the present method, the usage of the first reagent can be reduced by about 70% to about 90%, and the usage of the second reagent can be reduced by about 60% to about 75%, and thus using of the present method and reagent tube can reduce the detecting cost effectively and economic burden to the detector. For example, the reagent R1 usage for the prior detecting of glycosylated hemoglobin is 1.2 ml, while the current usage is 0.16 ml now, reducing by 86%; the reagent R2 usage for the prior detecting is 0.2 ml, while the current usage is 0.07 ml now, reducing by 66%.

In addition, the retainer of the invention can be used repeatedly, it only needs to replace the colorimetric glass for each detecting, and meanwhile the production cost of the reagent tube is reduced.

BRIEF DESCRIPTION OF ACCOMPANYING DRAWINGS

FIG. 4 is a structural schematic view for the cap according to one embodiment of the invention;

FIG. 5 is a schematic view in cross-section for the cap shown in FIG. 4;

FIG. 6 is a structural schematic view in cross-section for the cap according to another embodiment of the invention;

FIG. 7 is a structural schematic view in cross-section for the cap according to yet another embodiment of the invention;

DETAILED DESCRIPTION OF INVENTION

In the following, the method and reagent tube for reducing reagent usage provided in the present invention will be explained in detail with reference to the accompanying figures.

Figure 3:
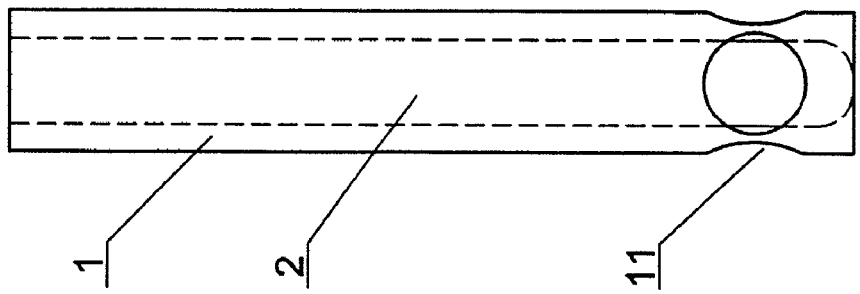
FIG. 3 is a structural schematic view when the calorimetric glass of the invention is inserted into the retainer.
Figure 2:
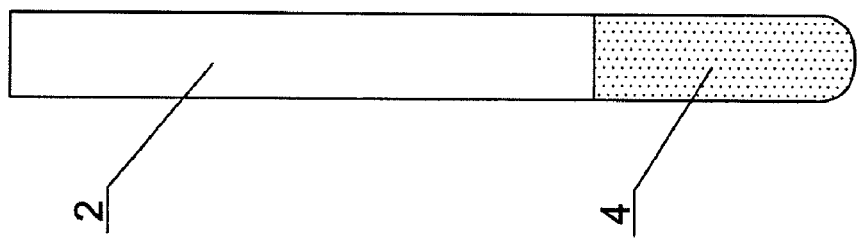
FIG. 2 is a structural schematic view for the colorimetric glass according to one embodiment of the invention.
Figure 1:
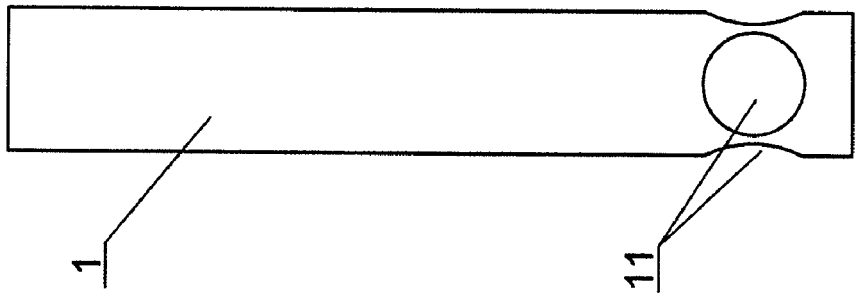
FIG. 1 is a structural schematic view for the retainer according to one embodiment of the invention.
Figure 9:
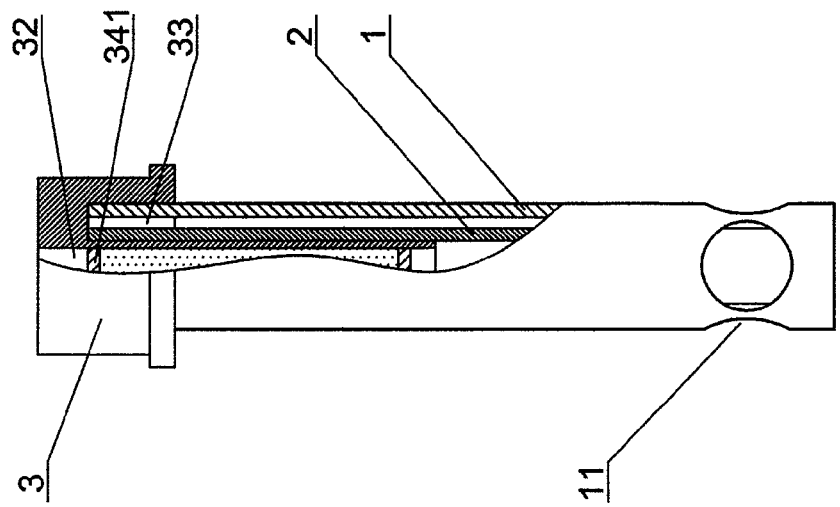
FIG. 9 is a cross-sectional view in partial of FIG. 8.
Figure 8:
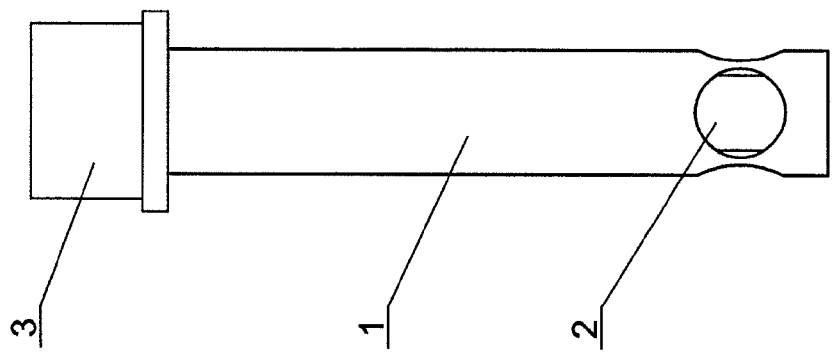
FIG. 8 is a structural schematic view when the retainer, calorimetric glass and cap of the invention are combined into a whole.

As shown in FIGS. 1-9, the reagent tube for reducing reagent usage provided in the present invention comprises:

a retainer 1, as shown in FIG. 1, the shape of said retainer 1 may be the same as that of the standard colorimetric tube generally used in an instruments, and the cross-section of which may be circular, rectangular or square (such as circular in the present embodiment), and at least one group of loopholes 11 is provided on the sidewalls of said retainer 1, generally speaking, loopholes 11 are provided at a position adjacent to the bottom of the sidewalls;

a calorimetric glass 2, as shown in FIG. 2, for receiving a first reagent 4, the dimension of said calorimetric glass 2 is smaller than that of the retainer 1, such that said calorimetric glass is adapted to be inserted into said retainer 1 (as shown in FIG. 3), and the reagent in the colorimetric glass 2 is observable through said loopholes 11;

a cap 3, for capping the colorimetric glass 2 and the retainer 1 into a whole after the calorimetric glass 2 is inserted into the retainer 1, as shown in FIGS. 8 and 9.

Particularly, as shown in FIGS. 4 and 5, said cap 3 comprises a cap body 31, an inner tube 32 provided at the axis center of cap body 31 and penetrated through the cap body, and a recess 33 provided at the bottom of the cap body; the second reagent 5 is added in advance and sealed within the inner tube 32 by a sealing means 34, and the inner tube 32 is adapted to be inserted into the calorimetric glass 2; the dimension of said recess 33 matches the thicknesses of the upper edges of the colorimetric glass 2 and the retainer 1, such that the upper edges of the colorimetric glass 2 and the retainer 1 is received in said recess 33 (as shown in FIG. 9).

Generally, in practical operation, the colorimetric glass 2 is firstly inserted into the retainer 1, then the inner tube 32 of the cap 3 is inserted into the calorimetric glass 2, and the upper edge of the colorimetric glass 2 is fixed with the upper edge of the retainer 1 by the recess 33, thus forming an integrated detecting reagent tube.

In addition, in order to reduce production cost, the gap 3 also may not be provided with said recess 33, as shown in FIG. 6, such arrangement can reduce the cost of die sinking to a certain degree. In addition, in order to meet the needs of the instrument and other usage, the cap 3 can also be in other variations, such as a groove 35 is provided on the top of the cap 3, as shown in FIG. 7.

In the present embodiment, the sealing means 34 may be rubber gaskets, as shown in FIG. 5, the number of the rubber gaskets 341, 342 is two, and the rubber gaskets are provided at the positions adjacent to the top and bottom of the inner tube 32, respectively. In practical usage, so long as pressure is applied on the rubber gasket 341 adjacent to the top of the inner tube 32, the rubber gasket 342 adjacent to the bottom of the inner tube 32 slips down until falling into the calorimetric glass 2, and thus the second reagent 5 enters the colorimetric glass 2, and mixes with the mixture of the first reagent and the pre-treated blood.

In one embodiment of the invention (as shown in FIGS. 1, 8 and 9), said loopholes 11 are in two groups, each group of loopholes 11 comprises two loopholes, and the projections projected in the axial direction of the said two loopholes are superposed, and preferably, the extension lines of said axis centers of said two groups of loopholes are perpendicular to each other.

In other embodiments of the invention, said loopholes 11 may also be in three groups, each group of loopholes 11 also comprises two loopholes, and the projections projected in the axial direction of the said two loopholes are superposed, and preferably, the extension lines of said axis centers of said three groups of loopholes 11 form an angle of 60° with each other. Likewise, the number of groups of loopholes of the invention may also be in other cases, such as one group or four groups, as required by the instrument.

In the present invention, the material of the retainer 1 may be polytetrafluoroethylene, metal or hard plastic, and the colorimetric glass 2 may be of transparent material, such as UV-transmitting plastic, quartz group material or light-transmitting plastic.

In addition, in the product formed by the invention, said colorimetric glass 2 may also have a cap (not shown) when releasing, so as to prevent being polluted during transportation; moreover, one or more collision objects (not shown), such as small steel balls, may be further provided in said calorimetric glass 2 in order to improve the homogeneity while mixing the reagents and reduce the operation time of mixing.

According to the above reagent tube for reducing reagent usage, the invention also provides a method for reducing reagent usage comprising the steps of:

providing a retainer 1, at least one group of loopholes 11 being provided on the sidewalls of said retainer 1;

providing a colorimetric glass 2 adapted to be inserted into said retainer 1, for receiving a first reagent to be observed through the said loopholes 11; and providing a cap 3, for capping the colorimetric glass 2 and the retainer 1 into a whole, after the colorimetric glass 2 be inserted into the retainer 1.

All of the retainer 1, colorimetric glass 2 and the cap 3 in the method and reagent tube for reducing reagent usage provided in the present invention are the same with the retainer 1, the colorimetric glass 2 and the cap 3 in the above embodiment; therefore, details are omitted here.

In the following, taking a particular embodiment of practical detecting of glycosylated hemoglobin as an example, the process of using the reagent tube of the invention will be described in detail again.

Firstly, open the cap of the colorimetric glass 2, add appropriate pre-treated blood sample to mix with the R1 reagent added in advance in the colorimetric glass 2, then insert the calorimetric glass 2 into the retainer 1, and close the cap 3 to form a reagent tube to be detected. Place the reagent tube into the Diazyme Smart340 Instrument, and the instrument firstly mix homogeneously R1 reagent with the pre-treated blood in the reagent tube while stirring, and because of the small steel ball, the reagents can be mixed quickly. After homogeneous mixing, use light rays of two wavelengths (340 nm and 700 nm) to carry on colorimetric detecting to the reagents in the calorimetric glass 2 through two groups of loopholes 11, and make records after obtaining calorimetric data. Hereinafter, press the sealing means (rubber gasket 341) in the cap 3 to make the R2 reagent in the gap 3 enter the colorimetric glass 2, and the instrument mixes the reagents homogeneously again, and because of the small steel ball, the reagents can be mixed quickly; after homogeneous mixing, use light rays of two wavelengths (340 nm and 700 nm) to carry on colorimetric detecting to the reagents in the colorimetric glass 2 through two groups of loopholes 11, and make records after obtaining colorimetric data.

Seen from the above description, the present invention mainly uses a reagent tube with a new structure of a retainer, a colorimetric glass and a cap, storing the first reagent only in the colorimetric glass, and the volume of the colorimetric glass is far less than that of the current reagent tube, thus the usage of the first reagent can be reduced greatly; and because the second reagent needs to mix with the first reagent in a certain proportion, thus the usage of the second reagent also can be reduced greatly. After comparison with experiments, it can reduce the usage of the first reagent by 70% to 90%, the usage of the second reagent by 60% to 75%, and thus can reduce the detecting cost effectively and economic burden to the detector. Taking the detecting of glycosylated hemoglobin in the above embodiment as an example, the inner diameter of the reagent tube in the prior art is generally 10 mm, and 1.2 ml of the first reagent (R1 reagent) and 0.2 ml of the second reagent (R2 reagent) are needed in the detecting; but with the technical solution of the present invention, the inner diameter of the colorimetric glass is only 5.2 mm, and only 0.16 ml of the first reagent (R1 reagent) and 0.07 ml of the second reagent (R2 reagent) are needed in the detecting, that is, reducing the first reagent by 86% and the second reagent by 66%, respectively.

In addition, the retainer of the invention can be used repeatedly, it only needs to replace the colorimetric glass for each detecting, and meanwhile the production cost of the reagent tube can be reduced.

What is claimed is:

1. A reagent tube for reducing reagent usage, said reagent tube comprising:
    a retainer with sidewalls,
    at least one group of loopholes provided on the sidewalls of the retainer;
    a colorimetric glass adapted to be inserted in said retainer, said colorimetric glass adapted to receive a first reagent to be observed through said loopholes; and
    a cap adapted to enclose the colorimetric glass within the retainer after the colorimetric glass is inserted
    wherein said cap comprises
    a cap body having an axis center;
    an inner tube pre-loaded with a second reagent and sealed with a seal, said inner tube being provided at the axis center of the cap body and penetrating through the cap body, wherein the inner tube is adapted to be inserted into the colorimetric glass; and
    a recess provided at the bottom of the cap body, the dimension of said recess matches the thicknesses of the upper edges of the colorimetric glass and the retainer, such that the upper edges of the colorimetric glass and the retainer are received in said recess.

2. A reagent tube for reducing reagent usage according to claim 1, wherein said seal comprises two rubber gaskets, provided at positions adjacent to the top and bottom of the inner tube respectively.

3. A reagent tube for reducing reagent usage according to claim 1, wherein said loopholes are in two groups, and each group of the loopholes comprises two loopholes, and projections projected in an axial direction of the said two loopholes are superimposed.

4. A reagent tube for reducing reagent usage according to claim 1, wherein the material of said retainer is polytetrafluoroethylene, metal or hard plastic, and said colorimetric glass is of a transparent material selected from the group consisting of UV-transmitting plastic, quartz group material, and light-transmitting plastic.

5. A method for reducing reagent usage, comprising:
    providing a reagent tube according to claim 1;
    filling a reagent to be detected into the reagent tube; and
    detecting the reagent through at least one group of the loopholes.

6. A method for reducing reagent usage according to claim 5, wherein said loopholes are in two groups, and each group of loopholes comprises two loopholes, and projections projected in the axial direction of the said two loopholes are superimposed.

7. A method for reducing reagent usage, comprising
    providing a reagent tube according to claim 1;
    filling a reagent to be detected into the reagent tube;
    pre-loading the second reagent in advance and sealing the second reagent in the inner tube;
    inserting the pre-loaded inner tube into the colorimetric glass;
    matching the dimension of said recess with the thicknesses of the upper edges of the colorimetric glass and the retainer, such that the upper edges of the colorimetric glass and the retainer are received in said recess; and
    detecting the reagent through at least one group of the loopholes.

8. A method for reducing reagent usage according to claim 7, wherein said sealing is accomplished by a seal that comprises two rubber gaskets, provided at positions adjacent to the top and bottom of the inner tube respectively.

\* \* \* \* \*

UNITED STATES PATENT AND TRADEMARK OFFICE
CERTIFICATE OF CORRECTION

Page 1 of 2

PATENT NO. : 8,246,920 B2
APPLICATION NO. : 12/503723
DATED : August 21, 2012
INVENTOR(S) : Yu et al.

It is certified that error appears in the above-identified patent and that said Letters Patent is hereby corrected as shown below:

In column 1 at line 23-24, Change "calorimetric" to --colorimetric--.

In column 1 at line 27, Change "calorimetric" to --colorimetric--.

In column 1 at line 29, Change "calorimetric" to --colorimetric--.

In column 1 at line 31, Change "calorimetric" to --colorimetric--.

In column 1 at line 48, Change "calorimetric" to --colorimetric--.

In column 1 at line 51, Change "calorimetric" to --colorimetric--.

In column 1 at line 57-58, Change "calorimetric" to --colorimetric--.

In column 2 at line 2-3, Change "calorimetric" to --colorimetric--.

In column 2 at line 33, Change "calorimetric" to --colorimetric--.

In column 2 at line 34, Change "calorimetric" to --colorimetric--.

In column 2 at line 62, Change "calorimetric" to --colorimetric--.

In column 3 at line 6, Change "calorimetric" to --colorimetric--.

In column 3 at line 27, Change "calorimetric" to --colorimetric--.

In column 3 at line 28, Change "calorimetric" to --colorimetric--.

In column 3 at line 29, Change "calorimetric" to --colorimetric--.

In column 3 at line 34, Change "calorimetric" to --colorimetric--.

In column 3 at line 42, Change "calorimetric" to --colorimetric--.

Signed and Sealed this
Ninth Day of April, 2013

Teresa Stanek Rea
*Acting Director of the United States Patent and Trademark Office*

CERTIFICATE OF CORRECTION (continued)
U.S. Pat. No. 8,246,920 B2

In column 3 at line 49, Change "calorimetric" to --colorimetric--.

In column 3 at line 67, Change "calorimetric" to --colorimetric--.

In column 4 at line 30, Change "calorimetric" to --colorimetric--.

In column 4 at line 56, Change "calorimetric" to --colorimetric--.

In column 4 at line 64, Change "calorimetric" to --colorimetric--.

In column 4 at line 65, Change "calorimetric" to --colorimetric--.

In column 6 at line 33, In Claim 7, after "comprising" insert --:--.